(12) United States Patent
Wesp et al.

(10) Patent No.: US 8,419,437 B2
(45) Date of Patent: Apr. 16, 2013

(54) DEVICE FOR THE DETERMINATION OF PARAMETERS PARTICULARLY FOR THERAPEUTIC COMPRESSION MEANS ON LIMBS

(75) Inventors: Hansjoerg Wesp, Koenigsbronn (DE); Ulrich Oestreicher, Eschwege (DE); Harald Jung, Kreimbach-Kaulbach (DE)

(73) Assignee: Paul Hartmann AG, Heidenheim (DE)

( * ) Notice: Subject to any disclaimer, the term of this patent is extended or adjusted under 35 U.S.C. 154(b) by 937 days.

(21) Appl. No.: 11/658,100

(22) PCT Filed: Jul. 15, 2005

(86) PCT No.: PCT/EP2005/007695
§ 371 (c)(1),
(2), (4) Date: Oct. 6, 2008

(87) PCT Pub. No.: WO2006/012986
PCT Pub. Date: Feb. 9, 2006

(65) Prior Publication Data
US 2009/0215016 A1    Aug. 27, 2009

(30) Foreign Application Priority Data

Jul. 30, 2004 (DE) .......................... 10 2004 038 421

(51) Int. Cl.
*G09B 23/28* (2006.01)
(52) U.S. Cl.
USPC ......................................... 434/267; 434/262
(58) Field of Classification Search .................. 434/268, 434/274, 262
See application file for complete search history.

(56) References Cited

U.S. PATENT DOCUMENTS

| | | | |
|---|---|---|---|
| 2,675,703 A | | 4/1954 | Hemmerich |
| 3,755,920 A | * | 9/1973 | Smrcka .......................... 434/274 |
| 3,792,243 A | * | 2/1974 | Appel et al. ................... 345/473 |
| 3,818,756 A | | 6/1974 | Barron |
| 4,000,564 A | * | 1/1977 | Haffner et al. ................ 434/274 |
| 4,276,032 A | * | 6/1981 | Woley et al. .................. 434/274 |
| 4,349,339 A | * | 9/1982 | Daniel .......................... 434/274 |
| 4,350,490 A | * | 9/1982 | Sandegard .................... 434/274 |
| 4,464,123 A | * | 8/1984 | Glover et al. ................. 434/268 |
| 4,605,373 A | * | 8/1986 | Rosen ........................... 434/274 |
| 4,683,669 A | * | 8/1987 | Greer, Jr. ........................ 40/414 |
| 4,850,877 A | * | 7/1989 | Mason et al. ................. 434/274 |
| 5,062,856 A | * | 11/1991 | Sawamura et al. ............. 623/24 |
| 5,282,460 A | * | 2/1994 | Boldt ............................... 601/5 |
| 5,413,611 A | * | 5/1995 | Haslam et al. ................. 623/25 |
| 5,476,441 A | * | 12/1995 | Durfee et al. .................. 602/23 |
| 5,589,651 A | * | 12/1996 | Viano et al. .................. 73/866.4 |
| 5,840,047 A | * | 11/1998 | Stedham ....................... 600/587 |

(Continued)

FOREIGN PATENT DOCUMENTS

GB          2 168 156         11/1986

*Primary Examiner* — Robert J Utama
(74) *Attorney, Agent, or Firm* — Paul Vincent

(57) ABSTRACT

A device for the determination of parameters, particularly for therapeutic compression measures on limbs (10), comprises an anatomically-modelled limb (10), to which the compression measures may be applied, with sensors (42), provided on the limb (10), for recording said parameter. The surface (44) of the limb (10) is at least partially elastically-deformable in at least one direction and at least one simulation device for a muscle (22, 24) is provided in the limb (10), which may be controlled to give a merely partial deformation of the surface (44) of the limb (10).

13 Claims, 3 Drawing Sheets

U.S. PATENT DOCUMENTS

| | | | |
|---|---|---|---|
| 5,853,292 A * | 12/1998 | Eggert et al. | 434/262 |
| 5,853,293 A * | 12/1998 | Weber et al. | 434/262 |
| 5,888,213 A * | 3/1999 | Sears et al. | 623/24 |
| 5,945,056 A * | 8/1999 | Day et al. | 264/250 |
| 6,198,247 B1 * | 3/2001 | Barr | 318/568.1 |
| 6,220,922 B1 * | 4/2001 | Lee et al. | 446/383 |
| 6,319,011 B1 * | 11/2001 | Motti et al. | 434/262 |
| 6,334,363 B1 | 1/2002 | Testud | |
| 6,500,210 B1 * | 12/2002 | Sabolich et al. | 623/24 |
| 6,532,400 B1 * | 3/2003 | Jacobs | 700/245 |
| 6,638,073 B1 * | 10/2003 | Kazimirov et al. | 434/272 |
| 6,669,483 B1 * | 12/2003 | Leight et al. | 434/262 |
| 6,695,770 B1 * | 2/2004 | Choy et al. | 600/38 |
| 6,773,263 B2 * | 8/2004 | Nicholls et al. | 434/267 |
| 6,790,043 B2 * | 9/2004 | Aboud | 434/268 |
| 6,923,081 B2 * | 8/2005 | Krstic | 73/866.4 |
| 6,991,510 B2 * | 1/2006 | Nan | 446/220 |
| 7,073,112 B2 * | 7/2006 | Chai et al. | 714/733 |
| 7,113,848 B2 * | 9/2006 | Hanson | 700/245 |
| 7,255,565 B2 * | 8/2007 | Keegan | 434/272 |
| 7,353,151 B2 * | 4/2008 | Furusu et al. | 703/11 |
| 7,384,268 B2 * | 6/2008 | Browne-Wilkinson | 434/274 |
| 7,427,199 B2 * | 9/2008 | Sakezles | 434/267 |
| 7,597,017 B2 * | 10/2009 | Bedard et al. | 73/866.4 |
| 2002/0061504 A1 * | 5/2002 | Saijo et al. | 434/268 |
| 2002/0106619 A1 * | 8/2002 | Farenholtz et al. | 434/262 |
| 2003/0018388 A1 * | 1/2003 | Comer | 623/14.13 |
| 2003/0120183 A1 * | 6/2003 | Simmons | 600/595 |
| 2004/0126746 A1 * | 7/2004 | Toly | 434/262 |
| 2004/0254771 A1 * | 12/2004 | Riener et al. | 703/7 |
| 2006/0051728 A1 * | 3/2006 | Browne-Wilkinson | 434/267 |
| 2008/0021570 A1 * | 1/2008 | Bedard et al. | 623/40 |
| 2009/0011394 A1 * | 1/2009 | Meglan et al. | 434/268 |
| 2010/0136510 A1 * | 6/2010 | Sakezles | 434/274 |
| 2010/0192394 A1 * | 8/2010 | Cheng Tam et al. | 33/2 R |

* cited by examiner

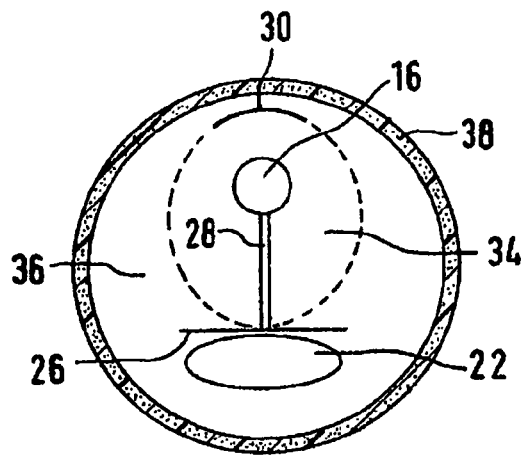
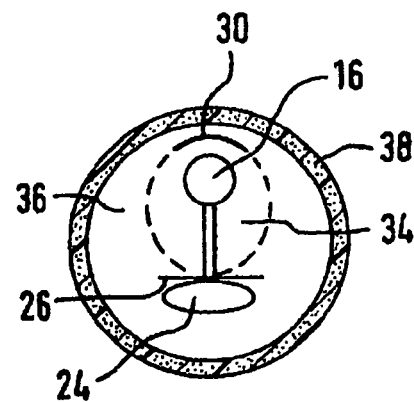
Fig. 2  Fig. 3
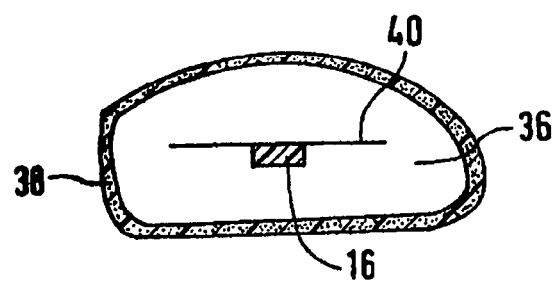
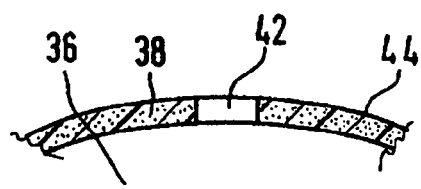
Fig. 4  Fig. 5

DEVICE FOR THE DETERMINATION OF PARAMETERS PARTICULARLY FOR THERAPEUTIC COMPRESSION MEANS ON LIMBS

This application is the national stage of PCT/EP2005/007695 filed on Jul. 15, 2005 and also claims Paris Convention priority of DE 10 2004 038 421.5 filed on Jul. 30, 2004.

BACKGROUND OF THE INVENTION

The invention concerns a device for determining parameters of, in particular, therapeutical compression means on limbs, comprising an anatomically modelled limb to which the compression means can be mounted, wherein the limb has sensors for receiving the parameters to be determined.

Compression means of this type may e.g. be so-called "compression socks" or "compression tights", in general socks or tights having a certain supporting effect, but also corresponding, mostly tubular structures for the arm region, where such measures are used e.g. after breast operations in order to prevent or treat accumulation of liquid in the arms. Such compression means may also be obtained using flat materials, such as e.g. bandages or dressing material, which are applied to the desired limb for compression. These products are mainly knitted fabrics, wherein it is decisive for the success of the therapy, that the pressure on the body surface is sufficient but not too high. The level of compression pressure depends, in particular, on the properties of the material, the processing or production technology and the technique of application. The measurement of parameters, in particular, the applied compression or pressure is advantageous for the production or development of such compression means, but may also be used e.g. to train patients wearing such compression means, or to train the medical and therapeutical staff. The point pressures that result in dependence on the radius of the underlying structure can be theoretically calculated through tensile force relationships of a specific compression material and application of the Laplace formula. This applies to cylindrical and rigid bodies.

A plurality of rigid systems of this type have been described in prior art. U.S. Pat. No. 6,334,363 B1 describes e.g. a device for measuring pressure points through therapeutical compression means, wherein a plurality of sensors are provided which are disposed on the surface of the rigid mold that corresponds to a leg. A pressure profile of the compression means can be generated through simultaneous measurement of the pressures at all measuring points and the plurality of measuring points.

U.S. Pat. No. 4,137,763 moreover discloses a rigid system which also detects pressure values at a plurality of measuring points.

The lower leg or arm of a person, which are the main fields of application of the compression means, are neither cylindrical nor rigid. Depending on the characteristics of the muscles and the mobility of the upper ankle joint or knee, the muscle bellies are shifted during muscle contraction, e.g. during running/walking. This leads to a dynamic system, wherein the perimeters on the lower leg change approximately cyclically with each step.

This influences the resulting pressures under a compression means which change in accordance with the step cycle. When the muscle is relaxed, this is called a resting pressure and when it is contracted, a working pressure. The ratio between resting and working pressures of a compression means is the value which is decisive and characteristic for the clinical efficiency of the therapy.

EP 1 118 851 A1 discloses e.g. a first approach for improving such devices, which discloses a device for measuring the compression through hosiery, wherein a lower rump is provided from individual tubular elements which are partially formed from shells, wherein the shells can be spread apart in order to model legs having a varying thickness in their longitudinal direction. In this fashion, initial elastic properties of hosiery can be measured. However, the model of anatomical movement is disadvantageously oversimplified due to the individual tubular elements, and simulation of a motion sequence by mechanically opening the tubular segments is also inadequate.

GB 2,168,156 A1 also discloses spreading apart, however, for adjusting the measuring body to hosiery to be measured.

In another conventional fashion, measurements concerning the dynamic pressure behavior are performed on human beings by disposing pressure sensors onto the skin. The patients were provided with a corresponding compression were instructed to run on a running belt while the pressures were continuously measured. Such measurements are indeed close to practice but can normally only be reproduced or transferred with great difficulty.

Due to the fact that there is great variance between the two legs of a single person, from day to day, or even throughout the day, even repeated measurements can approach the precise desired value in vivo to only a limited degree.

It is therefore the object of the invention to provide a device of the above-described type which permits reproducible, quasi-continuous measurement of pressures of compression means both in a static and also dynamic fashion.

SUMMARY OF THE INVENTION

The invention thereby solves the object with a device of the above-described type, wherein the surface of the limb can at least be partially elastically deformed in at least one direction and at least one muscle simulation means is provided in the limb, which can be driven such that the surface of the limb is only partially deformed.

In this fashion, the human limb can be realistically modelled with maximum precision. When the limb is a leg, the outer shape of the limb may be modelled like a standard leg (standard sizes of manufacturers of hosiery and also other conventional sizes for producing a leg that maximally resembles a human leg). A model may have, in particular, one or two muscle simulation means, in particular, in the area of the peroneal muscles (musculus triceps surae, musculus gastrocnemius and/or musculus soleus). When an arm is to be modelled, e.g. biceps and triceps may be modelled. The limb may thereby not be completely modelled but e.g. only part of the limb, such as the lower arm or the lower leg. Complete limbs may also be alternatively produced.

In order to obtain a particularly good model of a limb, at least two muscle simulation means may be provided, each causing only partial deformation of the limb surface. It may thereby be interesting that the at least two muscles can be driven not simultaneously but at least partially independently and, in particular, in an alternating fashion, such that they imitate muscle contraction or relaxation or simulate motions, such as running/walking. This imitation of muscle relaxation or contraction causes partial deformation of the surface of the limb.

At least part of the simulation means may thereby be driven independently and, in particular, alternatingly, and not all muscle simulation means at the same time, wherein driving thereof produces partial deformation of the surface of the limb.

The muscle simulation means may thereby comprise a hollow body whose volume and/or shape can be changed, wherein the volume and/or shape change is effected through emptying or filling the hollow body, and partial deformation of the surface of the limb is caused by the different fill levels. The muscle simulation means may thereby, in particular, be filled with air or liquid via hoses. The elasticity of the surface materials thereby permits extension of the thickness of the limbs in the area above the simulated muscles. All relaxation or contraction states of the imitated muscle can be simulated in this fashion. The cover of the hollow body may thereby also be elastic. When further materials are provided between the modelled muscle and the surface of the limb, these may also be elastic.

The overall volume and volume flow of the air or liquid may also be adjusted. In this fashion, the speed and the degree of volume displacement during muscle contraction can be adjusted.

A system of this type has the following further advantages in addition to the above-mentioned advantages. In addition to quality control in the production of corresponding compression means, a system of this type may also be used for quality control after extensive strain or for aged or otherwise modified materials. Moreover, a corresponding system may be used for developing new compression materials or combinations and for direct comparison of products. Further possible applications are the physiological characterization of compression materials and also quality control in attendance and application, since e.g. nurses and also patients can directly control the success of the application technique. In this fashion, the efficiency of the therapeutical measure can be improved. The surface of the limb may thereby be covered with a synthetic skin. Such synthetic skins are usually used as surfaces for prosthetics. Simulation means for bones and/or soft tissue and/or joints may also be provided. The heel may e.g. be modelled in the foot area using wood and metal elements. A simulation means for the shinbone may also be provided.

The simulation means for the soft tissue may be silicone elements, wherein silicones with different elasticity coefficients are used. The overall shape, except for technically required components such as feed lines, bones and muscle elements, may be completely produced from silicone or mixtures or different silicones. It may e.g. be produced by initially using sectional drawings e.g. of a standard leg (standard dimensions from hosiery producers) and converting these sectional drawings to the "50th percentile individual". The individual sectional drawings are then glued onto rigid foam discs in order to produce a model, are cut out, the disks are fixed on top of each other, and the transitions are smoothed. A negative shape of gypsum is then produced from the rigid foam model and silicone is cast into the negative mold, leaving recesses for the components. The components, such as e.g. hollow bodies for the muscles, rods and further simulation means for bones etc. are then installed. The outer structure, i.e. the synthetic skin is subsequently disposed. The silicone may be silicone of the trademark Elastosil of the company Wacker-Chemie GmbH, which, in its hardened state, may be selected due to its processing properties, viscosity and material properties. It may also be designed in a layered structure from different centrically structured silicone layers.

In a preferred example of the invention, the layered structure is formed from silicones of different hardnesses. A silicone of a hardness Shore A of more than 15 (DIN 53505) may e.g. be used inside the device, whereas the layer disposed on the inner layer comprises a silicone of a hardness Shore A of less than 15 (DIN 53505). The simulation means for the muscle(s) is thereby, in particular, surrounded by a silicone of a higher elasticity and mechanical solidity.

The sensors may be embedded under the synthetic skin or in skin substitute material. At the respective locations, the skin substitute material may e.g. be punched out to accommodate the sensors, in particular, Piezo pressure sensors. The cables and feed lines or branching off for data transport may be disposed below the artificial skin and be connected to an evaluation unit in such a fashion that the detected data can be used for further processing and/or visualization and/or storage. A suitable number and amount of sensors are thereby mounted to the limb.

The limb may moreover comprise one or more regions, in particular, joint regions which are used to simulate movable joints. This is particularly advantageous for hosiery which must be designed, in particular, for the compression properties in the transition area between leg and foot, or between lower leg and upper leg or in the hip area or brachial joints.

Finally, means may also be provided in the limb which enlarge the overall circumference of the limb such that the limb can be adjusted to fluctuations of the human structure that occur e.g. during the day, from day to day or between the different seasons and temperatures.

Further advantages and features of the invention can be extracted from the accompanying disclosure. The invention is explained in more detail below with reference to a drawing.

BRIEF DESCRIPTION OF THE DRAWING

FIG. 2 shows a section through FIG. 1 along line II-II;

FIG. 3 shows a section through FIG. 1 along line III-III;

FIG. 4 shows a section through FIG. 1 along line IV-IV;

FIG. 5 shows an enlarged schematic view of the surface of a limb; and

DESCRIPTION OF THE PREFERRED EMBODIMENT

Figure 1:
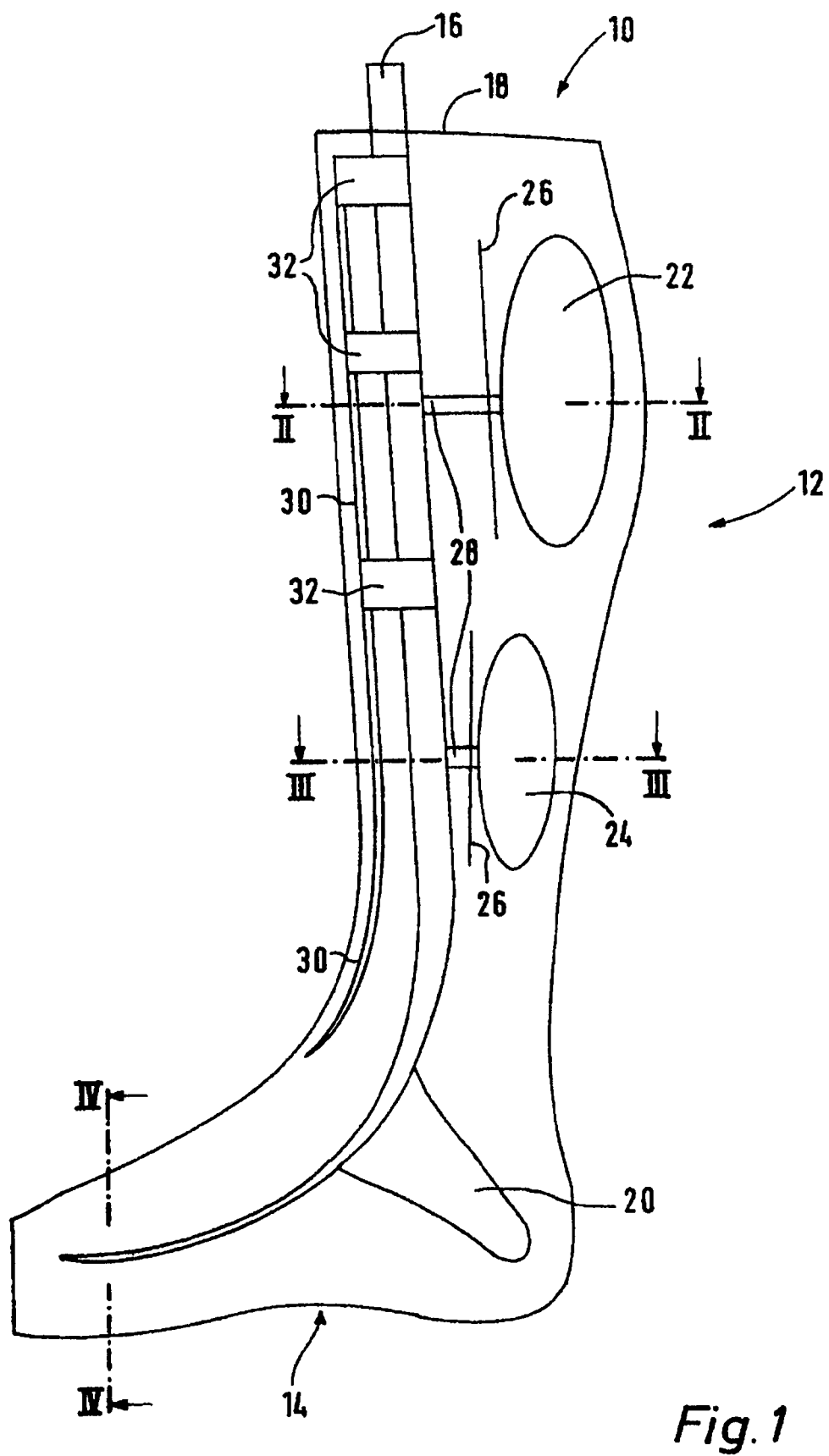
FIG. 1 shows a schematic sectional view of a limb of the inventive device in the form of a lower leg.

FIG. 1 shows a limb, i.e. a lower leg, having an anatomically modelled shape, wherein the existing data is determined, standardized and then transferred to the present model in order to simulate the limb of the leg of a person. The limb 10 thereby comprises a calf area 12 and a foot area 14. The connection between the calf area 12 and the foot area 14 of the present model is inflexible, i.e. there are no simulation means for a joint. A supply tube 16 extends through the overall limb 10, which enters into the limb 10 at the upper edge 18 of the limb 10 and extends to the foot area 14. The supply tube 16 is used for supply (explained below) of the simulation means for the muscles 22, 24 and of the sensors and also to stabilize the limb 10. The supply tube 16 thereby tapers in the area of the foot 14 where it fulfils merely a holding function in the present limb design, since the present design does not include detection of compression means with respect to working pressure in the area of the foot 14. The supply tube 16 has a rectangular cross-section in the area of the foot 14, and a round cross-section in the area of the lower leg 12.

The supply tube 16 is disposed in the area of the front side of the calf area, i.e. close to the shin of a person.

The supply tube 16 also serves to hold further components of the device. A wooden element is e.g. mounted in a heel area, as a simulated heel bone 20, in order to stabilize the foot shape of the device.

The limb also has two hollow spaces 22 and 24 whose walls are formed from an air-impermeable elastic material. The hollow spaces are defined by two compressed air cushions of the company Pronal-Leers (FR). The hollow spaces 22 and 24 serve as simulation means for muscles, in the present case, the two main calf muscles. The hollow bodies 22 and 24 may thereby have different volumes.

Figure 6:
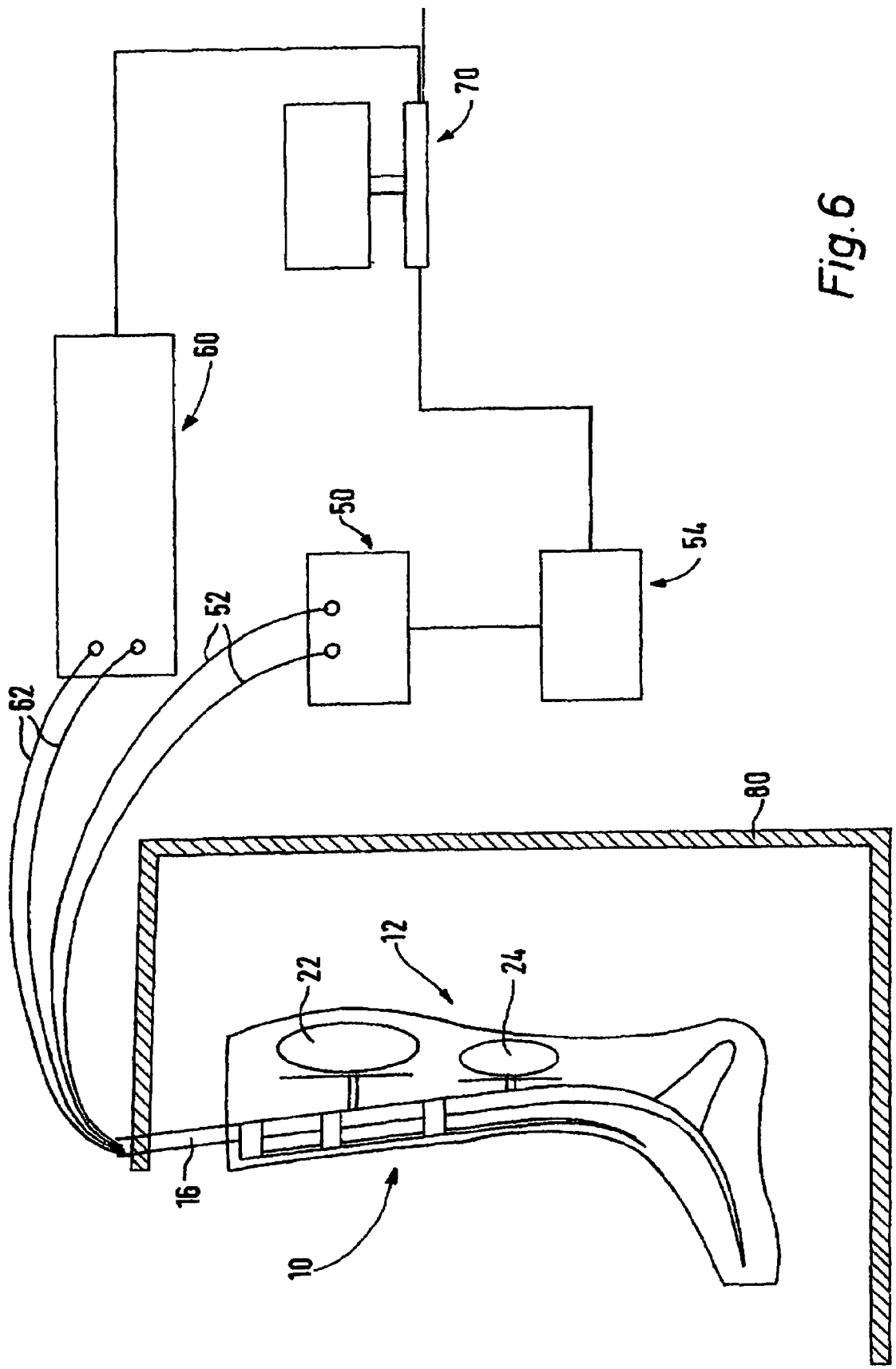
FIG. 6 shows a device in accordance with FIG. 1 with the associated control and evaluation unit.

The two muscles 22 and 24 that are simulated by the models are those muscles which are responsible for deformation of the calf area 12 (musculus gastrocnemius and musculus soleus) of a lower leg when a person is walking. The hollow bodies 22 and 24 are connected via holding plates 26 and supply tubes 28 to the supply tube 16. Air supply and discharge lines are guided in the supply tube 16 and in the supply tubes 28, which permit filling and emptying of the hollow spaces 22 and 24. Filling is thereby performed mostly alternatingly between the two hollow spaces to optimally simulate a walking sequence. The feed and discharge lines for air filling may thereby be connected to an external compressor 50 (FIG. 6). A simulation means for a shin 30 is moreover connected to the supply tube 16, which extends in correspondence with a human shin in the front edge area across the length of the extremity. Holding means 32 are provided for holding the shin model 30, each connecting the shin model 30 to the supply tube 16.

FIGS. 2 through 5 illustrate the construction of the limb in more detail. FIG. 2 shows a section along line II-II, wherein the supply tube 16 is disposed eccentrically in the front area of the limb. At a certain separation from the supply tube 16, the shin imitation 30 is disposed towards the front edge, i.e. the shinbone of the artificial limb 10. However, the supply tube 28 extends from the supply tube 16 towards the calf, and on to the hollow space 22 that is fixed to the holding plate 26 and coupled there to the supply tube 28. The holding plate 26 may thereby be coated with a foam material. The supply tube 16 and the supply tube 28, including a first soft tissue simulation means 34 which is formed from a first silicone (Elastosil M 3500 company Wacker Chemie GmbH (DE)) and extends, at least in the calf area 12, over the length of the limb 10, are thereby located between the shin model 30 and the holding plate 26. The first soft tissue simulation means 34 may thereby be produced from a first silicone material having a first elasticity coefficient. This first silicone material moreover protects and stabilizes the supply tube 16 and the supply tube 28. The first silicone arrangement 34 moreover supports the simulated shin 30.

The remaining volume of the device is then filled with a further silicone material 36 (Elastosil M 4511 company Wacker Chemie GmbH (DE)) which also serves as simulation means for soft tissue. The second silicone material 36 may thereby be less stable but more elastic and deformable than the first silicone material 34. The outer surface of the device is then formed by a synthetic skin 38 (Softtouch—covering sock, Otto Bock—Duderstade (DE)) which completely surrounds the device. FIG. 3 is thereby correspondingly structured.

Only a holding plate 40 for the foot is provided in the area of the foot 14, wherein this is a model for a left foot which can be seen from the different instep heights on the supply tube 16 which consists substantially of a solid material in this case. A silicone material 37 (Elastosil M 4511 company Wacker Chemie GmbH (DE)) is provided in the foot area, which has an even greater stability than the first silicone material 34.

FIG. 5 shows a design of the skin 38, which is an artificial skin that is usually used for the artificial limb. A piece of the artificial skin 38 is thereby punched out for inserting sensors 42 (pressure sensors company Gisma GmbH-Buggingen (DE)) in the present case a sensor, in particular, a Piezo pressure sensor, such that the surface of the sensor 42 is flush with the surface 44 of the artificial skin 38. The electric supply and the data lines are guided below the artificial skin 38, in particular, between the artificial skin 38 and the silicone 36, and introduced into the supply tube 16 at a suitable location.

FIG. 6 shows the complete device arrangement for measuring the compression e.g. of a compression sock that extends to the knee. The compression sock (not shown) is thereby pulled over the limb 10, like a person wearing this compression sock would put it on. The above-described sensors 42 are thereby distributed over the artificial skin, at least in the overall calf area 12 of the limb 10. The electric supply and also the line for the data to be recorded thereby extends initially to an A/D converter 60, and from there, further to a computer-supported evaluation unit 70.

As described above, a compressor 50 is also provided which is connected to the muscle models 22 and 24 via lines 52. The muscle models 22 and 24 are driven via a compressor control 54 which is responsible for alternatingly filling and emptying the modelled muscles 22 and 24. The walking sequence is simulated by the amount and the time sequence of filling and emptying. In addition to detecting the static pressure in the resting state of the leg, the dynamic pressure distribution of the therapeutical compression means can also be measured, in the present case the compression sock. It is measured through the values determined by the sensors 42, which they pass on to the evaluation unit 70 via data lines 62 and the A/D converter. The compressor control 54 is also connected to the evaluation unit 70.

The limb 10 may be suspended on a frame 80 via its supply tube 16, in order to eliminate any influence on the motion of the calf area 12 due to influences of a support.

The determined values for the compression means may then be illustrated, stored and further processed in the evaluation unit 70.

We claim:

1. A method for determining parameters of a therapeutical compression element on a limb, the method comprising the steps of:
    a) preparing an anatomically modeled limb, the limb having a surface which is structured for elastic deformation in at least one direction, the limb also having at least one muscle simulation element disposed within the limb and at least one sensor mounted at the surface of the limb;
    b) mounting a therapeutical compression element on the limb, the compression element thereby cooperating with and exerting an inwardly directed compression pressure on the surface of the limb;
    c) activating the muscle simulation element using a driving element, the muscle simulation element thereby partially deforming the surface of the limb and inducing a change in the compression pressure exerted by the compression element on the surface of the limb which simulates contraction and relaxation of the muscle; and
    d) measuring, using the sensor element, the change in compression pressure generated in step c).

2. The method of claim 1, wherein at least two muscle simulation elements each cause only one partial deformation of said surface of said limb.

3. The method of claim 2, wherein said at least two muscle simulation elements cannot be driven simultaneously, rather at least partially independently.

4. The method of claim 3, wherein said at least two muscle simulation elements are driven in an alternating fashion.

5. The method of claim 1, wherein said muscle simulation element comprises a hollow body whose volume or shape can be changed, and which can be emptied or filled for changing said volume or said shape, wherein different fill levels partially deform said surface of said limb.

6. The method of claim 1, wherein said muscle simulation element is hydraulically or pneumatically driven.

7. The method of claim 1, wherein said surface of said limb is formed by a synthetic skin.

8. The method of claim 1, wherein said limb further comprises a bone simulation element, a soft tissue simulation element, or a joint simulation element.

9. The method of claim 8, wherein said soft tissue simulation element is produced from one or more silicones.

10. The method of claim 7, wherein said at least one sensor is disposed below or embedded into said synthetic skin.

11. The method of claim 1, wherein said limb comprises one or more areas which simulate corresponding joints.

12. The method of claim 1, wherein said limb comprises an element for enlargement of an overall perimeter thereof.

13. The method of claim 1, wherein said surface can be elastically deformed in a circumferential direction or in all directions.

* * * * *